United States Patent
Bowen et al.

(10) Patent No.: US 10,923,291 B2
(45) Date of Patent: Feb. 16, 2021

(54) OXIDE ON EDGES OF METAL ANODE FOILS

(71) Applicant: PACESETTER, INC., Sunnyvale, CA (US)

(72) Inventors: David R. Bowen, Taylors, SC (US); Ralph Jason Hemphill, Sunset, SC (US)

(73) Assignee: Pacesetter, Inc., Sunnyvale, CA (US)

(*) Notice: Subject to any disclaimer, the term of this patent is extended or adjusted under 35 U.S.C. 154(b) by 186 days.

(21) Appl. No.: 15/959,065

(22) Filed: Apr. 20, 2018

(65) Prior Publication Data

US 2018/0240603 A1 Aug. 23, 2018

Related U.S. Application Data

(62) Division of application No. 14/992,712, filed on Jan. 11, 2016, now Pat. No. 9,978,529.

(51) Int. Cl.
| | | |
|---|---|---|
| *H01G 9/055* | (2006.01) | |
| *H01G 9/045* | (2006.01) | |
| *H01G 9/00* | (2006.01) | |
| *H01G 9/26* | (2006.01) | |
| *A61N 1/39* | (2006.01) | |
| *C25F 3/04* | (2006.01) | |

(Continued)

(52) U.S. Cl.
CPC .......... *H01G 9/055* (2013.01); *A61N 1/3956* (2013.01); *H01G 9/0032* (2013.01); *H01G 9/045* (2013.01); *A61N 1/3968* (2013.01); *C23F 1/16* (2013.01); *C25F 3/04* (2013.01); *H01G 9/26* (2013.01)

(58) Field of Classification Search
CPC .......... H01G 9/045; H01G 9/042; H01G 9/035
See application file for complete search history.

(56) References Cited

U.S. PATENT DOCUMENTS

| 3,622,843 A | 11/1971 | Vermiyea |
|---|---|---|
| 3,779,877 A | 12/1973 | Alwitt |

(Continued)

FOREIGN PATENT DOCUMENTS

| JP | 59083772 | 5/1984 |
|---|---|---|
| JP | 02075155 | 3/1990 |

(Continued)

OTHER PUBLICATIONS

Non-Final Office Action dated Nov. 3, 2004, Related U.S. Appl. No. 10/680,777.

(Continued)

*Primary Examiner* — Eric W Thomas (57) ABSTRACT

A capacitor and a method of processing an anode metal foil are presented. The method includes electrochemically etching the metal foil to form a plurality of tunnels. Next, the etched metal foil is disposed within a widening solution to widen the plurality of tunnels. Exposed surfaces of the etched metal foil are then oxidized. The method includes removing a section of the etched metal foil, where the section of the etched metal foil includes exposed metal along an edge. The section of the etched metal foil is placed into a bath comprising water to form a hydration layer over the exposed metal on the section of the etched metal foil. The method also includes assembling the section of the etched metal foil having the hydration layer as an anode within a capacitor.

18 Claims, 6 Drawing Sheets

(51) Int. Cl.
*C25F 1/16* (2006.01)
*C23F 1/16* (2006.01)

(56) References Cited

U.S. PATENT DOCUMENTS

| | | | |
|---|---|---|---|
| 3,872,579 | A | 3/1975 | Papadopoulos |
| 4,213,835 | A | 7/1980 | Fickelscher |
| 4,266,332 | A | 5/1981 | Markarian et al. |
| 4,420,367 | A | 12/1983 | Locher |
| 4,474,657 | A | 10/1984 | Arora |
| 4,481,084 | A | 11/1984 | Chen et al. |
| 4,518,471 | A | 5/1985 | Arora |
| 4,525,249 | A | 6/1985 | Arora |
| 4,541,037 | A | 9/1985 | Ross et al. |
| 4,593,343 | A | 6/1986 | Ross |
| 4,663,824 | A | 5/1987 | Kenmochi |
| 4,696,082 | A | 9/1987 | Fonfia |
| 4,758,929 | A | 7/1988 | Naitoh et al. |
| 4,975,806 | A * | 12/1990 | Clouse ............... H01G 9/022 361/505 |
| 5,131,388 | A | 7/1992 | Pless et al. |
| 5,175,227 | A | 12/1992 | Gardon et al. |
| 5,230,962 | A | 7/1993 | Stephenson |
| 5,522,841 | A | 6/1996 | Roby et al. |
| 5,522,851 | A | 6/1996 | Fayram |
| 5,602,198 | A | 2/1997 | Das et al. |
| 5,660,737 | A | 8/1997 | Elias et al. |
| 5,663,240 | A | 9/1997 | Simeone et al. |
| 5,715,133 | A | 2/1998 | Harrington et al. |
| 6,168,706 | B1 | 1/2001 | Hemphill et al. |
| 6,224,738 | B1 | 5/2001 | Sudduth et al. |
| 6,377,442 | B1 * | 4/2002 | Strange ............... H01G 9/00 361/508 |
| 6,426,864 | B1 | 7/2002 | O'Phelan |
| 6,686,124 | B1 | 2/2004 | Angelopoulos et al. |
| 6,736,956 | B1 | 5/2004 | Hemphill et al. |
| 6,802,954 | B1 | 10/2004 | Hemphill et al. |
| 6,858,126 | B1 | 2/2005 | Hemphill et al. |
| 7,452,473 | B1 | 11/2008 | Hemphill et al. |
| 7,531,078 | B1 * | 5/2009 | Strange ............... C25F 3/04 205/661 |
| 7,578,924 | B1 | 8/2009 | Jiang et al. |
| 7,745,281 | B2 | 6/2010 | Prymak et al. |
| 8,535,507 | B1 | 9/2013 | Hemphill et al. |
| 8,734,964 | B2 | 5/2014 | Kurihara et al. |
| 8,888,967 | B2 | 11/2014 | Hemphill et al. |
| 9,275,800 | B2 | 3/2016 | Ribbie et al. |
| 9,412,525 | B2 | 8/2016 | Bowen et al. |
| 2002/0111029 | A1 | 8/2002 | Johnson |
| 2002/0191371 | A1 | 12/2002 | Lessner et al. |
| 2006/0046417 | A1 | 3/2006 | Kobayashi et al. |
| 2010/0024182 | A1 | 2/2010 | Shimamoto et al. |
| 2010/0053847 | A1 * | 3/2010 | Tani ............... H01G 9/035 361/505 |
| 2012/0026645 | A1 | 2/2012 | Sakakura et al. |

FOREIGN PATENT DOCUMENTS

| | | |
|---|---|---|
| JP | 04056309 | 2/1992 |
| JP | 07049428 | 2/1995 |
| KR | 102015034009 A * | 4/2015 |
| WO | 2000/04-06 | 4/2000 |

OTHER PUBLICATIONS

Patel et al., "A New Coating Process for Aluminum", Posted on Oct. 25, 2000 on http://www.ceramicindustry.com. Downloaded from http://www.ceramicindustry.com/CDA/ArticleInformation/Features/BNP_Features_Item/0.270,13674.00.html on Oct. 21, 2004.
Amendment filed Mar. 3, 2005; Related U.S. Appl. No. 10/680,777.
Final Office Action dated May 23, 2005; Related U.S. Appl. No. 10/680,777.
English Translation of JP 059-083772 performed by USPTO Translator Akiko Smith.
Notice of Appeal dated Sep. 23, 2005; Related U.S. Appl. No. 10/680,777.
Amendment filed Sep. 23, 2005; Related U.S. Appl. No. 10/680,777.
Notice of Allowance dated Sep. 24, 2008; Related U.S. Appl. No. 10/940,793.
Amendment filed Aug. 28, 2008; Related U.S. Appl. No. 10/940,793.
Examiner Interview Summary dated Aug. 1, 2008; Related U.S. Appl. No. 10/940,793.
Amendment filed Jun. 30, 2008; Related U.S. Appl. No. 10/940,793.
Final Office Action dated Mar. 28, 2008; Related U.S. Appl. No. 10/940,793.
Amendment filed Jan. 7, 2008; Related U.S. Appl. No. 10/940,793.
Non-Final Office Action dated Oct. 5, 2007; Related U.S. Appl. No. 10/940,793.
Amendment filed Sep. 21, 2007; Related U.S. Appl. No. 10/940,793.
Final Office Action dated Jun. 21, 2007; Related U.S. Appl. No. 10/940,793.
Amendment filed Apr. 10, 2007; Related U.S. Appl. No. 10/940,793.
Non-Final Office Action dated Jan. 10, 2007; Related U.S. Appl. No. 10/940,793.

* cited by examiner

OXIDE ON EDGES OF METAL ANODE FOILS

CROSS REFERENCE TO RELATED APPLICATIONS

This application is a division of U.S. patent application Ser. No. 14/992,712, entitled Oxide on Edges of Metal Anode Foils, filed Jan. 11, 2016, incorporated herein by reference in its entirety to provide continuity of disclosure.

FIELD

The present invention relates generally to the field of electrochemical etching of anode foils for use in electrolytic capacitors.

BACKGROUND

Compact, high voltage capacitors are utilized as energy storage reservoirs in many applications, including implantable medical devices. These capacitors are required to have a high energy density, since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Implantable Cardioverter Defibrillators, such as those disclosed in U.S. Pat. No. 5,131,388, incorporated herein by reference, typically use two electrolytic capacitors in series to achieve the desired high voltage for shock delivery. For example, an implantable cardioverter defibrillator may utilize two 350 to 400 volt electrolytic capacitors in series to achieve a voltage of 700 to 800 volts.

Electrolytic capacitors are used in ICDs because they have the most nearly ideal properties in terms of size, reliability and ability to withstand relatively high voltage. Conventionally, such electrolytic capacitors include an etched aluminum foil anode, an aluminum foil or film cathode, and an interposed kraft paper or fabric gauze separator impregnated with a solvent-based liquid electrolyte. While aluminum is the preferred metal for the anode plates, other metals such as tantalum, magnesium, titanium, niobium, zirconium and zinc may be used. A typical solvent-based liquid electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent. The entire laminate is rolled up into the form of a substantially cylindrical body, or wound roll, that is held together with adhesive tape and is encased, with the aid of suitable insulation, in an aluminum tube or canister. Connections to the anode and the cathode are made via tabs. Alternative flat constructions for aluminum electrolytic capacitors are also known, comprising a planar, layered, stack structure of electrode materials with separators interposed therebetween, such as those disclosed in the above-mentioned U.S. Pat. No. 5,131,388.

In ICDs, as in other applications where space is a critical design element, it is desirable to use capacitors with the greatest possible capacitance per unit volume. Since the capacitance of an aluminum electrolytic capacitor is provided by the anodes, a clear strategy for increasing the energy density in the capacitor is to minimize the volume taken up by paper and cathode and maximize the number of anodes. A multiple anode stack configuration requires fewer cathodes and paper spacers than a single anode configuration and thus reduces the size of the device. A multiple anode stack consists of a number of units consisting of a cathode, a paper spacer, two or more anodes, a paper spacer and a cathode, with neighboring units sharing the cathode between them, all placed within the capacitor case.

Currently, etched/formed aluminum anode foil is punched by use of a mechanical die into an anode shape to conform to the necessary geometry of the capacitor case. In order to obtain higher capacitance, aluminum is removed from the anode foil during an etching process to create tunnels to increase surface area. A widening process is then used to open the tunnels to prevent clogging during a later oxide formation step. Both the etch and widening processes can remove as much as 50% to 60% of the aluminum to create greater than 30 million tunnels per $cm^2$. After the formation of the oxide, the foil becomes very brittle. The more aluminum removed (higher surface area), the harder the foil is to punch without creating cracks and particles.

After the anodes are punched by the mechanical die, the anodes are assembled into stacks with the paper and the cathode(s). The edges of the anodes can contain burrs and attached particles. The burrs and particles can penetrate the paper layer and cause a short circuit, which could compromise the quality and life of the capacitor.

Additionally, after the punching process, the newly created edges of the anodes have exposed aluminum without a high quality oxide formed thereon. After the assembly of the anodes, paper, and cathodes, the capacitor is sealed and impregnated with an electrolyte. Next, the capacitors are put through an aging process that forms oxide on the edges and any exposed cracks in the anodes, but the oxide formed from the aging process is not as high quality as the oxide formed during the formation process. The higher the edge area to anode surface area, the higher the leakage current of the capacitor. Additionally, the higher the edge area to anode surface area, the longer the aging process is required to be performed to form oxide on the edges.

BRIEF SUMMARY

A capacitor and method are presented that includes formation of a hydration layer on the etched anode foils before assembling the anode foils within the capacitor. Forming the hydration layer allows for a higher quality oxide to form on edges of the anode foils, which leads to reduced capacitor deformation, reduced leakage current, and increased lifetime.

According to an embodiment, a method of processing an anode metal foil includes electrochemically etching the metal foil to form a plurality of tunnels in the metal foil. Then, the etched metal foil is disposed within a widening solution, wherein the widening solution widens the plurality of tunnels in the metal foil. Exposed surfaces of the etched metal foil are then oxidized. The method includes removing a section (e.g., by stamping, shearing, or laser cutting) of the etched metal foil, that is to become the anode, from a remainder of the etched metal foil, where the removed section of the etched metal foil (i.e., the anode foil) includes exposed metal along one or more of its cut edges. The method includes placing the removed anode foil into a bath comprising water to form a hydration layer over the exposed metal on the cut edges of the anode foil. The method also includes assembling the anode foil with the hydration layer as an anode within a capacitor.

According to an embodiment, a method of processing an oxidized metal having exposed metal along one or more edges includes placing the oxidizing metal foil into a first bath comprising water to form a hydration layer over the exposed metal. Next, the oxidized metal foil having the hydration layer is placed into a second bath comprising ammonium dihydrogen phosphate. The method also includes assembling the oxidized metal foil having the hydration layer as an anode within a capacitor.

According to an embodiment, a capacitor includes a housing, one or more anodes disposed within the housing, one or more cathodes disposed within the housing, one or more separators disposed between an adjacent anode and cathode, and an electrolyte disposed around the one or more anodes, one or more cathodes, and one or more separators within the housing. The one or more anodes each include a metal that has a hydration layer formed before the one or more anodes are disposed within the housing. In one embodiment, the electrolyte includes less than 3% water content.

Further embodiments, features, and advantages of the present apparatus and method, as well as the structure and operation of the various embodiments of the present apparatus and method, are described in detail below with reference to the accompanying drawings.

BRIEF DESCRIPTION OF THE DRAWINGS/FIGURES

The accompanying drawings, which are incorporated herein and form part of the specification, illustrate the methods and systems presented herein for processing an anode metal foil. Together with the detailed description, the drawings further serve to explain the principles of and to enable a person skilled in the relevant art(s) to make and use the methods and systems presented herein. In the drawings, like reference numbers indicate identical or functionally similar elements. Further, the drawing in which an element first appears is typically indicated by the leftmost digit(s) in the corresponding reference number.

DETAILED DESCRIPTION

The following detailed description of methods and systems for processing metal anode foils refers to the accompanying drawings that illustrate exemplary embodiments consistent with these methods and systems. Other embodiments are possible, and modifications may be made to the embodiments within the spirit and scope of the methods and systems presented herein. Therefore, the following detailed description is not meant to limit the methods and systems described herein. Rather, the scope of these methods and systems is defined by the appended claims.

It would be apparent to one of skill in the art that the methods and systems for processing metal anode foils, as described below, may be implemented in many different embodiments without departing from the scope of the description below. Thus, the operation and behavior of the methods and systems will be described with the understanding that modifications and variations of the embodiments are possible, given the level of detail presented herein. It will be apparent to a person skilled in the relevant art that the methods and systems also be employed to produce porous anode foils for use in a variety of devices and applications in addition to use in an implantable cardioverter defibrillator (ICD).

Figure 1:
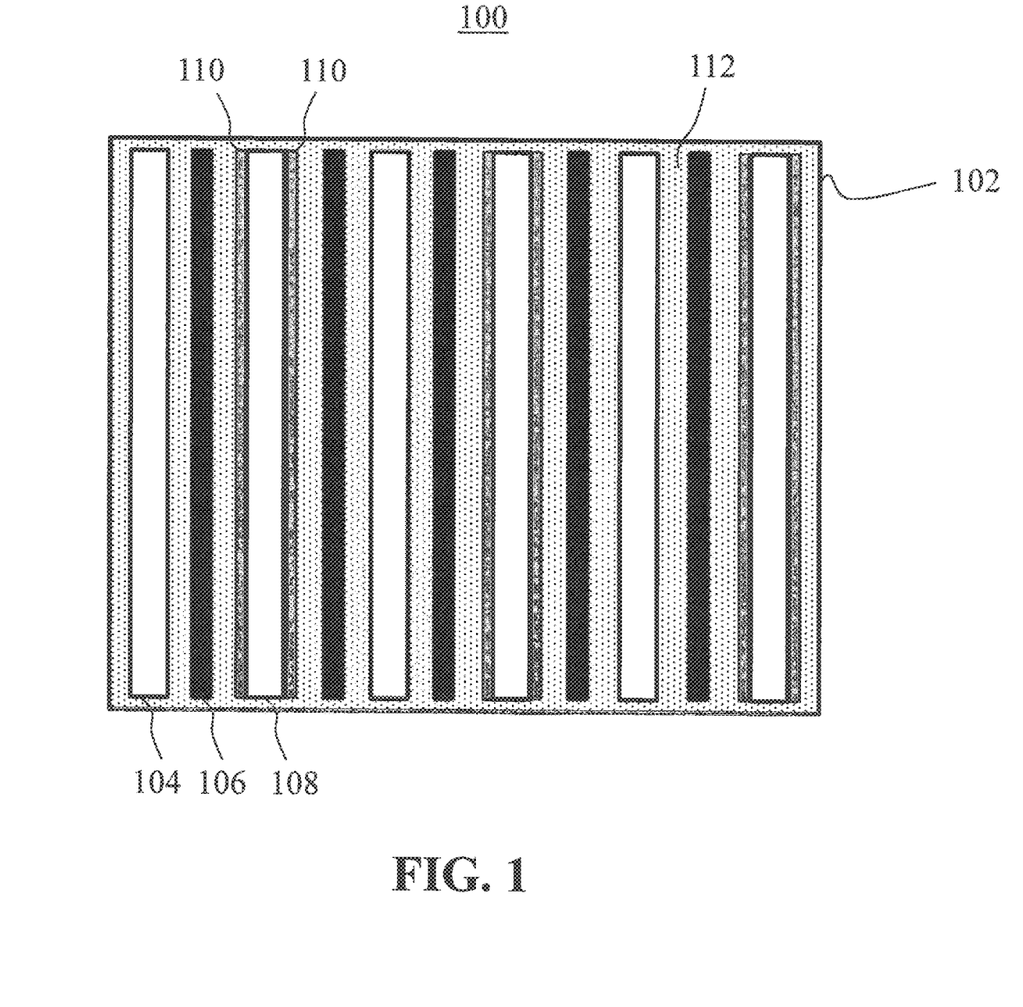
FIG. 1 illustrates a cross-section of an electrolytic capacitor or battery.

FIG. 1 illustrates a cross-section view of an electronic component 100. Electronic component 100 includes a housing 102 that contains a plurality of cathodes 104 alternating with a plurality of anodes 108, and separated by a plurality of separators 106. Each anode 108 includes a dielectric material 110 on or around an outer surface of anode 108. Dielectric material 110 may be an oxide that is thermally grown on, or deposited onto, the surface of anode 108. A high-k dielectric material may be used for dielectric material 110. A conductive electrolyte 112 fills the space between each of the elements within housing 102. Electrolyte 112 may be a polymer or liquid electrolyte as would be understood by one skilled in the art. Example electrolytes include ethylene glycol/boric acid based electrolytes and anhydrous electrolytes based on organic solvents such as dimethylformamide (DMF), dimethylacetamide (DMA), or gamma-butyrolactone (GBL). The plurality of cathodes 104 may be electrically connected to a single, common cathode terminal, and the plurality of anodes 108 may be similarly connected to a single, common anode terminal.

Electronic component 100 may be, for example, an electrolytic capacitor or a battery. When electronic component 100 is used as a capacitor, example materials for the plurality of cathodes 104 include aluminum, titanium, stainless steel, while example materials for the plurality of anodes 108 include aluminum and tantalum. When electronic component 100 is used as a battery, example materials for the plurality of cathodes 104 include silver vanadium oxide, carbon fluoride, magnesium oxide, or any combination thereof, while example materials for the plurality of anodes 108 include lithium metal.

Spacer 106 may be provided to maintain a given separation between each cathode 104 and an adjacent anode 108 within housing 102. Additionally, spacer 106 may be provided to prevent arcing between cathode 104 and anode 108 in spaces where dielectric 110 may be very thin or nonexistent, and/or where a void within electrolyte 112 exists between cathode 104 and anode 108.

It should be understood that the various elements and dimensions of electronic component 100 are not drawn to scale. Although each of capacitor 104, separator 106, and anode 108 are illustrated as being spaced apart from one another for the convenience of illustration and labeling, it would be understood by one skilled in the art that such elements may also be stacked together in close physical contact with one another.

Figure 2:
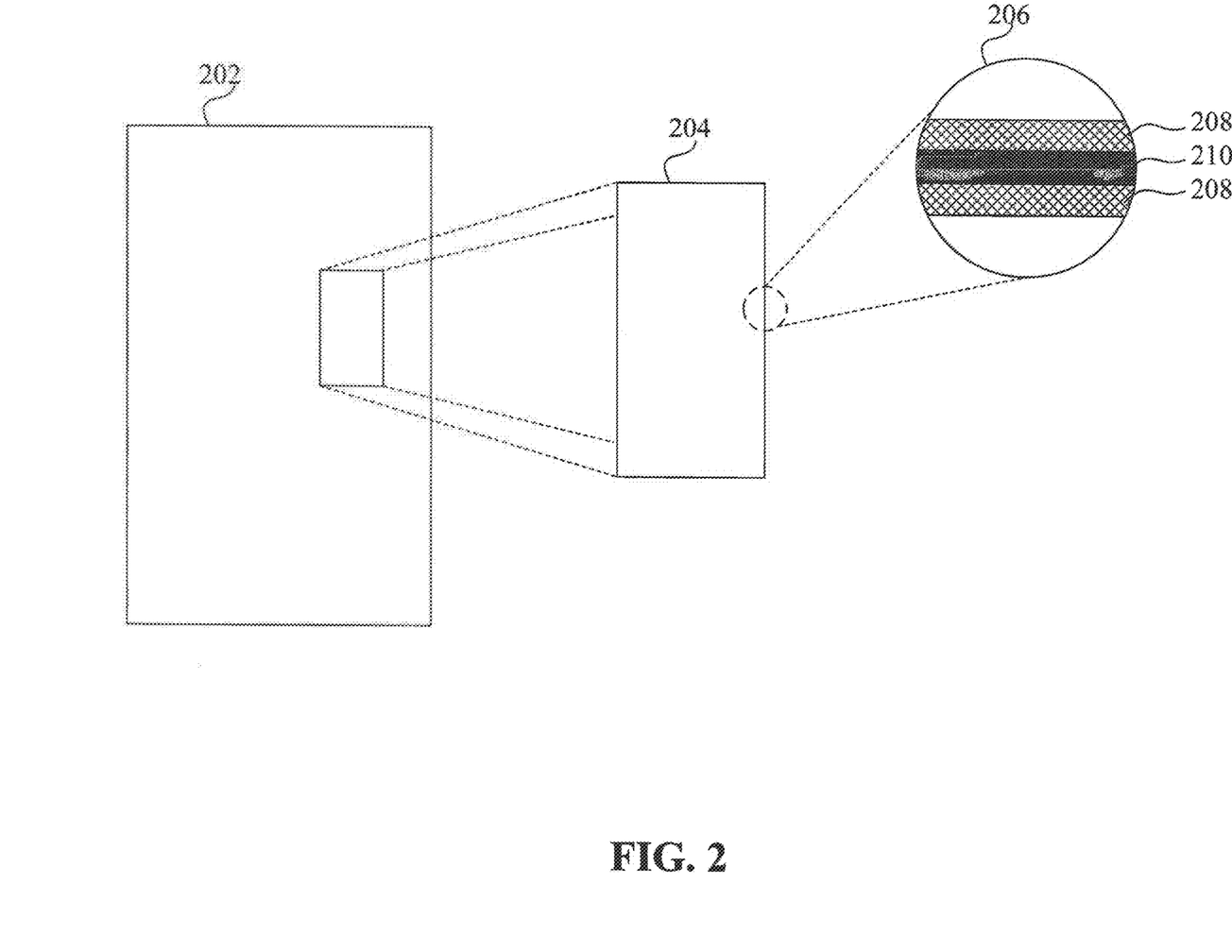
FIG. 2 illustrates the removal of an anode foil from a larger sheet, according to an embodiment.

FIG. 2 illustrates a process of removing a section (i.e., a portion) of a metal foil 204 from a larger metal sheet 202, according to an embodiment. Metal sheet 202 may be an aluminum sheet that has undergone electrochemical etching and widening processes to form pores that increase the surface area of metal sheet 202. Additionally, an oxidation process is performed to form an oxide over the exposed metal surfaces. In the case of an aluminum sheet, a thin layer of aluminum oxide may be formed over the exposed aluminum surface. Further details regarding the electrochemical drilling process may be found in U.S. Pat. Nos. 6,858,126, 6,802,954, and 8,535,507, the disclosures of which are incorporated by reference herein in their entireties.

Section 204 may be removed from the larger metal sheet 202 using any mechanical cutting, punching, or shearing method known in the art. Section 204 may also be removed from larger metal sheet 202 using laser cutting methods. When section 204 is removed from larger metal sheet 202, edges of section 204 will have exposed metal (e.g., metal not covered with dielectric 110.) An edge view 206 illustrates what an example edge of section 204 looks like when viewed on its side. Edge view 206 includes layers of metal oxide 208 on either side of metal 210. In the case where metal 210 is aluminum, metal oxide 208 may be aluminum oxide.

When section 204 is to be used as an anode within a capacitor, an aging process takes places to form an oxide over the exposed metal around the edges of section 204. This aging process uses water found in the electrolyte to form an oxide over the exposed metal at the edges. But this oxide is of a lower quality than the oxide formed over the larger surfaces of section 204. Additionally, the higher water content in the electrolyte needed to perform this aging process also leads to increased deformation during the life of the capacitor. The water can continue to react with the oxide and increase charge time as the oxide heals during charging after a given time period.

To address the shortcomings of prior methods, according to an embodiment, a hydration layer is first formed over the exposed metal of section 204 before section 204 is assembled within a capacitor, such as the capacitor illustrated in FIG. 1. The hydration process builds a non-voltage supporting hydration layer that helps to both create a higher quality oxide and speed up its formation during the aging process. The hydration process lowers the aging time by using a hydration oxide backbone to speed formation of the aging oxide. The hydration process also tends to clean up the edges from the punching process by "smoothing" any metal burrs on the edges of section 204, according to an embodiment. The detachment of the burrs and "smoothing" can be increased by use of sonic or ultrasonic vibrational energy when forming the hydration layer.

Figure 3:
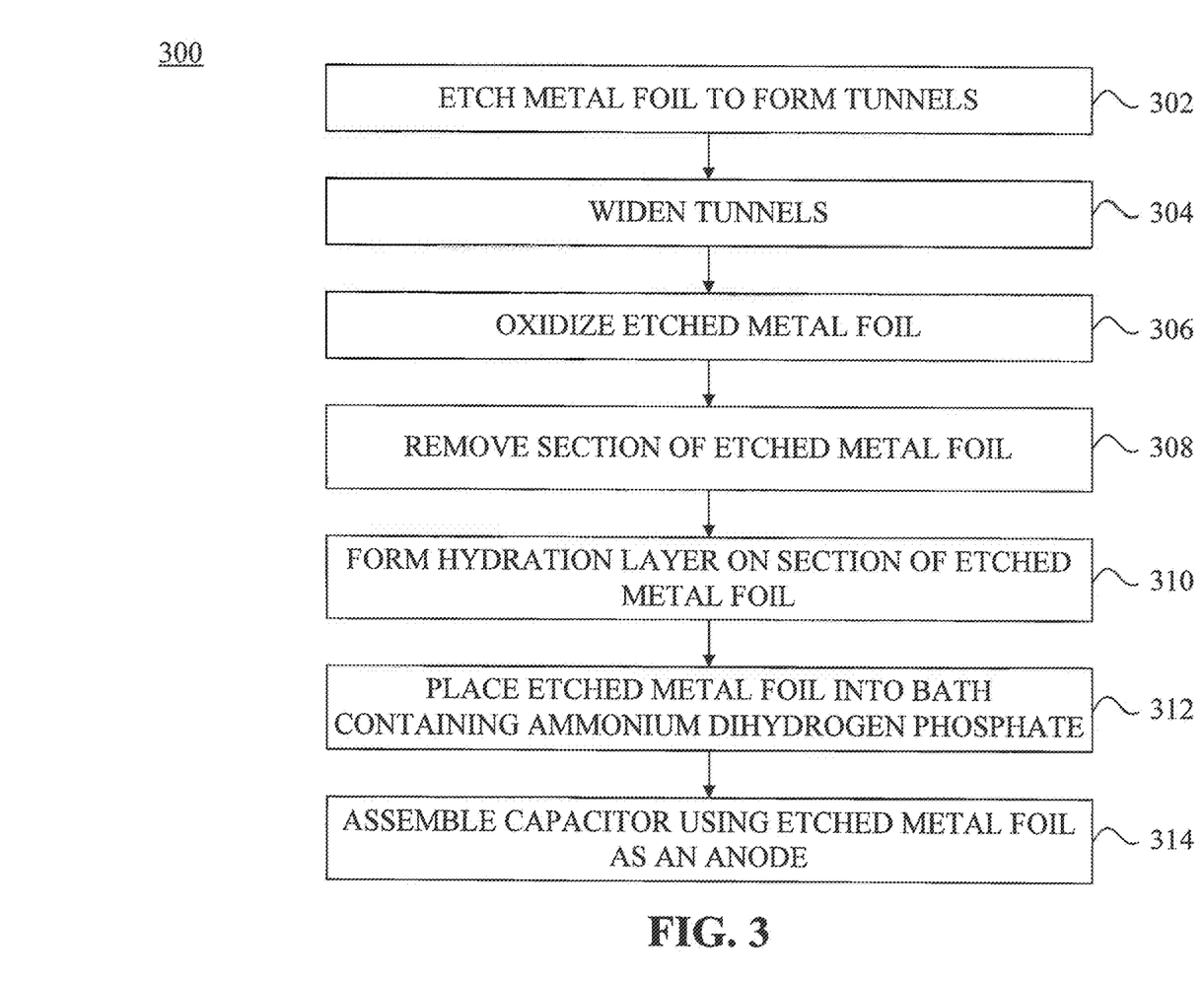
FIG. 3 is a flowchart of an example method of producing an anode foil.

FIG. 3 provides an example method 300 of producing an anode foil for use in a capacitor. Steps 302-306 generally describe the process for producing an oxidized and etched metal foil, from which the anode foil is punched out in step 306, according to an embodiment. It should be understood that other steps may be performed as well to produce the etched metal foil without limiting the embodiments described herein. Steps 310-312 generally describe the process of forming the hydration layer on the anode foil, before it is assembled within a capacitor in step 314.

In one embodiment, steps 302-306 are performed during one process cycle, while steps 308-312 are performed during a different process cycle, and step 314 is performed during yet another process cycle. For example, steps 302-306 may be performed to produce a plurality of etched, oxidized metal foils that may be taken to another work station, or stored in a protective area for a period of time, before performing steps 308-312. Similarly, the sections of etched metal foils having hydration layers may be taken to yet another work station, or stored in a protective area for a period of time, before they are assembled into a capacitor in step 314.

At step 302, a metal foil is etched to form a plurality of tunnels, or pores, within the metal foil. In one embodiment, the metal foil is an aluminum foil. At step 304, the tunnels formed in step 302 are widened to further increase the surface area of the etched metal foil. Note that steps 302 and 304 are not required for using the metal foil as an anode within a capacitor, however, they drastically increase the surface area and therefore the capacity and charge density of the capacitor. Examples of the etching and widening processes may be found in U.S. Pat. Nos. 6,858,126, 6,802,954, or 8,535,507.

At step 306, the etched metal foil is oxidized. In the case of an aluminum foil, a layer of aluminum oxide is formed over the exposed aluminum surface. Examples of the oxidization process may be found in U.S. Pat. Nos. 6,858,126, 6,802,954, or 8,535,507. During a standard process, the etched metal foil may be dipped into a bath containing ammonium dihydrogen phosphate to form a passivation layer over the etched metal foil at this step before any sections are removed from the etched metal foil. However, in the present embodiment, this phosphate dip should not occur before the hydration layer is formed as it can interfere with the formation of the hydration layer.

At step 308, a section is removed from the etched metal foil. The section may be, for example, mechanically cut, punched, or sheared from the etched metal foil, or cut via a laser. The section of etched metal foil may be sized to fit within a housing of a capacitor. As illustrated in FIG. 2, the section of etched metal foil will have exposed metal along one or more edges that were previously attached to the larger etched metal foil. For the remainder of method 300, the removed section of the etched metal foil will more simply be called the etched metal foil.

At step 310, a hydration layer is formed over the exposed metal on the etched metal foil, according to an embodiment. The etched metal foil may be placed into a bath containing water. In one example, the water is di-ionized. The bath of water may be held at a temperature between 60 and 100 degrees C., and preferably at about 95 degrees C. The etched metal foil may remain within the bath for anywhere between two and 20 minutes to form the hydration layer. In an embodiment, the bath of water is sonicated at either sonic or ultrasonic frequencies. The formation of the hydration layer will help to form a better quality oxide during the aging process, and also helps to reduce and/or smooth out the formation of burrs at the edges of the etched metal foil.

At step 312, the etched metal foil, now having a hydration layer, is placed into a separate bath that includes ammonium dihydrogen phosphate to form a passivation layer over the etched metal foil. Note that this step is not required, but will increase the lifetime of the capacitor. In an embodiment, the ammonium dihydrogen phosphate bath is maintained at a temperature between 50 and 90 degrees C., and preferably at about 70 degrees C. The bath contains between 0.1% and 5.0%, and preferably about 2.0%, by weight ammonium dihydrogen phosphate. The etched metal foil may be placed in the bath of ammonium dihydrogen phosphate for between one and four minutes. Afterwards, the etched metal foils may be removed from the bath of ammonium dihydrogen phosphate and rinsed under di-ionized water for between one and 12 minutes.

At step 314, the etched metal foil having the hydration layer is assembled within a capacitor as the anode, according to an embodiment. Any number of etched metal foils may be placed into the capacitor to form a single anode. An electrolyte is added to the capacitor that includes a water content below 3.0% by weight. In another example, the water content is between 0.6% and 3.0% in the electrolyte. A lower water content may be used in the electrolyte of capacitors designed using anodes with the hydration layer when compared to conventional capacitor designs. Using an electrolyte having a water content between 0.5% and 3.0% may reduce the deformation of the capacitor by about 10% when compared to higher water content electrolytes.

Figure 4A:
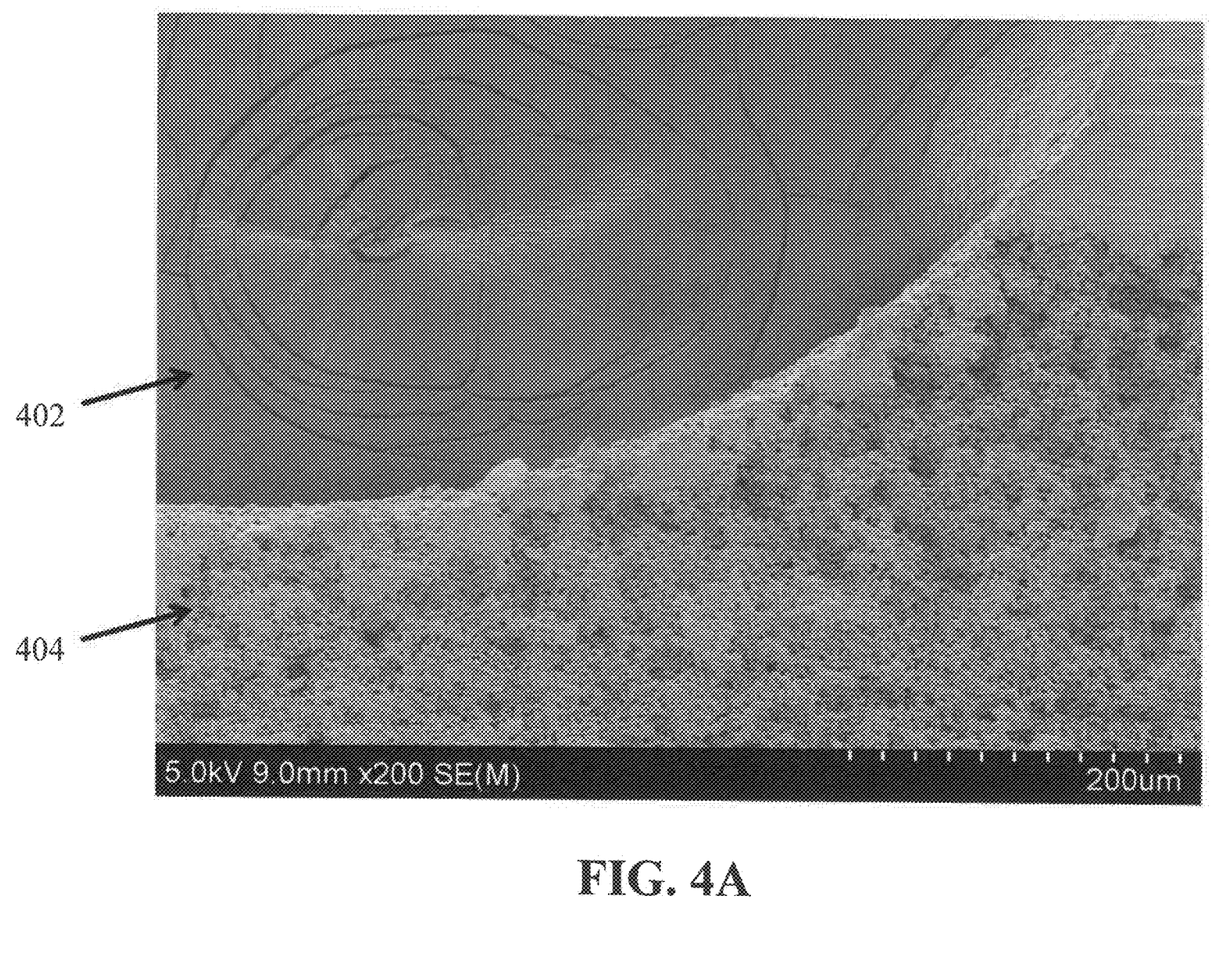
FIGS. 4A and 4B are SEM images of an anode foil surface before and after a hydration step, according to an embodiment.
Figure 4B:
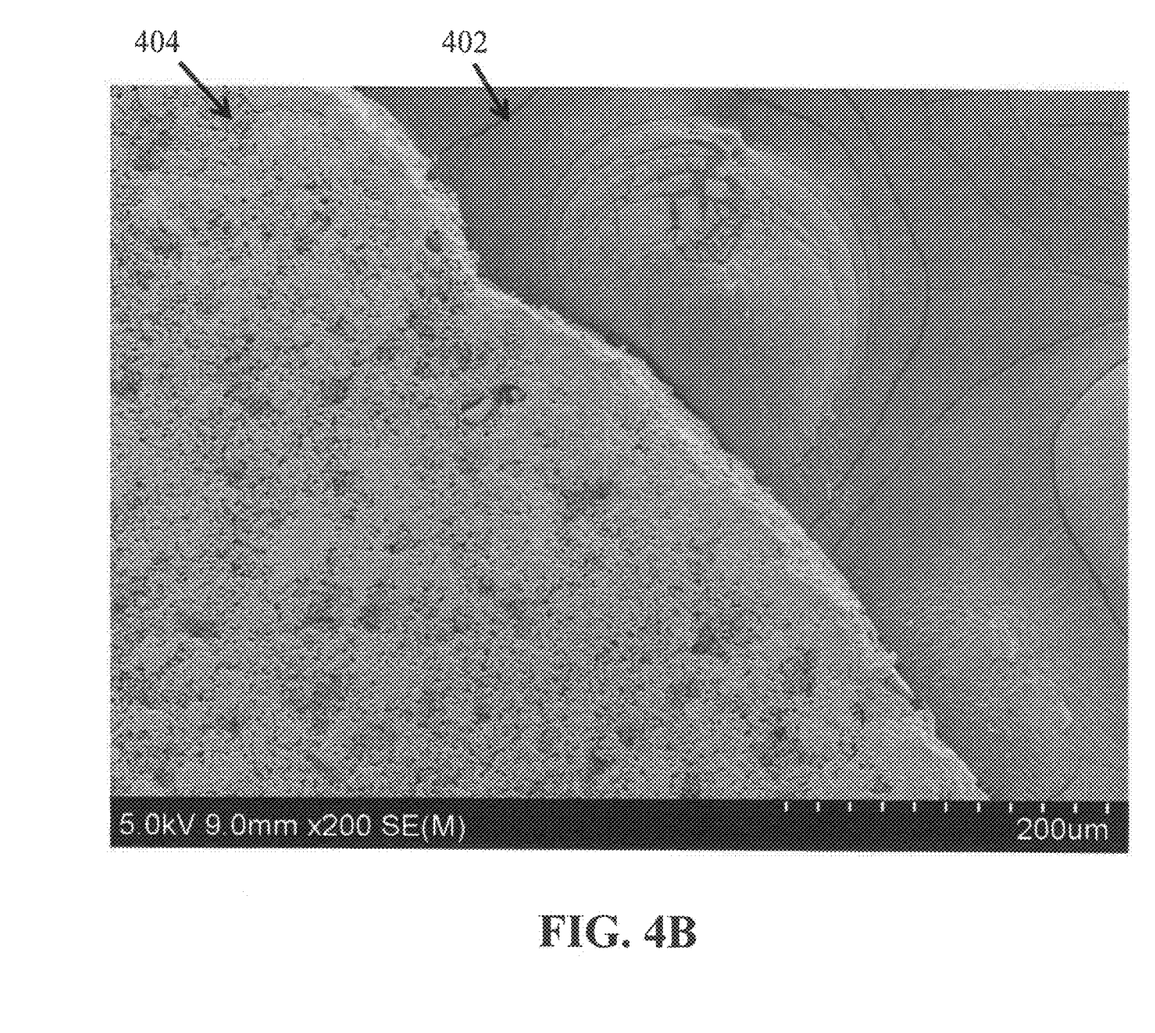

FIGS. 4A and 4B illustrate scanning electron microscope (SEM) images of an edge of an etched aluminum foil, according to some embodiments. These SEMs provide a glimpse of the edge of an etched aluminum foil, similar to the represented edge view 206 in FIG. 2. FIG. 4A illustrates a piece of tape 402 used to stabilize a layer of etched aluminum 404 before the formation of the hydration layer. Etched aluminum 404 is seen as having a rough surface with a plurality of burrs that can cause shorting problems in a final capacitor assembly. FIG. 4B illustrates etched aluminum 404 after the formation of the hydration layer over its exposed surface. The formation of the hydration layer creates a smoother surface and substantially reduces the number and/or size of burrs present on the surface.

Figure 5:
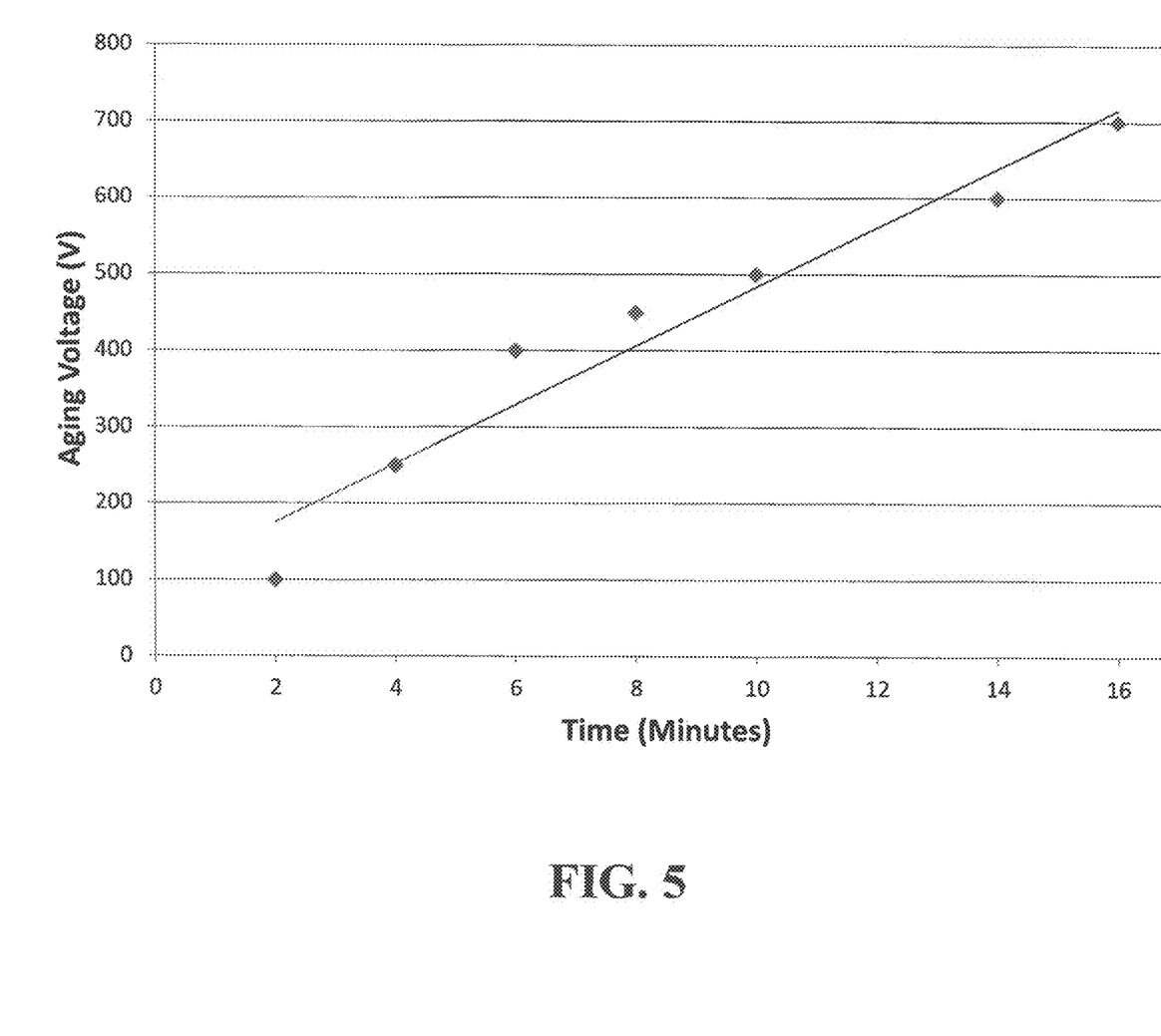
FIG. 5 is a graph illustrating capacitor aging voltage vs. hydration time.

The existence of the hydration layer over an aluminum anode foil also allows for a faster aging process when forming an oxide over the exposed aluminum surfaces. FIG. 5 illustrates an estimation of the time it takes to form a hydration layer on the aluminum anode foil for a given aging voltage. For lower aging voltages (less than 300 V), only a few minutes of aging are required to form a hydration layer that will facilitate a quality oxide growth.

In one example experiment, etched aluminum anodes were mechanically punched out of a sheet of foil and placed in a 95 deg. C. di-ionized water bath for eight minutes. After the hydration of the aluminum foil edges in the bath, the anodes were placed into a bath of ammonium dihydrogen phosphate at 70 deg. C. for four minutes, and afterwards, rinsed in di-ionized water for eight minutes. Next, the anodes were assembled into capacitors.

The capacitors had an eight cc volume with 28 anodes total in cathode/paper/anode layers with three to four anodes per layer. The capacitors were aged using a voltage of 425 V for a working nominal voltage in the final device of 400 Volts. The aging process up to the working voltage was between 5% and 10% faster due to the presence of the hydration layer, even when using an electrolyte having a relatively low water content (e.g., between 0.5% and 3%.) The leakage current after about five minutes of operation (and after holding the voltage at 400 Volts) was compared between capacitors with and without anodes formed with the hydration layer. The capacitor having the anodes without the hydration layer yielded a leakage current around 96.8 µA, while the capacitor having anodes with the hydration layer yielded a leakage current around 87.8 µA. The results of the experiment provided about a 9% reduction in the leakage current when using anodes with the hydration layer.

It is to be appreciated that the Detailed Description section, and not the Summary and Abstract sections, is intended to be used to interpret the claims. The Summary and Abstract sections may set forth one or more but not all exemplary embodiments of the present system and method as contemplated by the inventors, and thus, are not intended to limit the present method and system and the appended claims in any way.

Moreover, while various embodiments of the present system and method have been described above, it should be understood that they have been presented by way of example, and not limitation. It will be apparent to persons skilled in the relevant art(s) that various changes in form and detail can be made therein without departing from the spirit and scope of the present system and method. Thus, the present system and method should not be limited by any of the above described exemplary embodiments, but should be defined only in accordance with the following claims and their equivalents.

In addition, it should be understood that the figures, which highlight the functionality and advantages of the present system and method, are presented for example purposes only. Moreover, the steps indicated in the exemplary system(s) and method(s) described above may in some cases be performed in a different order than the order described, and some steps may be added, modified, or removed, without departing from the spirit and scope of the present system and method.

What is claimed is:

1. A capacitor, comprising:
   a housing;
   an anode foil within the housing, wherein the anode foil includes a hydration layer on a metal,
      the hydration layer being on an edge of the anode foil, and
      an oxide being on a face of the anode foil but not being between the edge of the anode foil and the hydration layer;
   a cathode foil within the housing; and
   a separator between the anode foil and the cathode foil.

2. The capacitor of claim 1, wherein the capacitor has a leakage current of about 87.8 µA.

3. The capacitor of claim 1, wherein the anode foil has a substantially reduced number of burrs relative to what the anode foil would have in the absence of the hydration layer.

4. The capacitor of claim 1, wherein the hydration layer contacts the metal.

5. The capacitor of claim 1, wherein the hydration layer includes a hydrate of the metal and the hydration layer contacts the metal.

6. The capacitor of claim 1, wherein an electrolyte is within the housing and the electrolyte has less than 3.0 wt % water.

7. The capacitor of claim 6, wherein the electrolyte includes water.

8. The capacitor of claim 7, wherein the electrolyte has between 0.5 wt % and 3.0 wt % water.

9. The capacitor of claim 1, wherein the oxide contacts an edge of the metal.

10. The capacitor of claim 1, wherein a second oxide is positioned on the edge of the anode foil, the second oxide being a different quality of oxide from the oxide is positioned on the face of the anode foil.

11. The capacitor of claim 1, wherein the anode foil includes a passivation layer.

12. The capacitor of claim 1, wherein the hydration layer does not support a voltage.

13. The capacitor of claim 1, wherein the hydrate layer includes a hydrate oxide backbone.

14. The capacitor of claim 1, wherein the metal is aluminum.

15. The capacitor of claim 1, wherein the oxide is an oxide of the metal.

16. The capacitor of claim 15, wherein the hydration layer includes a hydrate of the metal.

17. The capacitor of claim 16, wherein the oxide contacts the metal and the hydration layer contacts the metal.

18. The capacitor of claim 17, wherein the oxide contacts a face of the metal and the hydration layer contacts an edge of the metal.

* * * * *